United States Patent
Park et al.

(10) Patent No.: US 8,766,176 B2
(45) Date of Patent: Jul. 1, 2014

(54) SPECTRUM ACQUISITION MODES FOR ION MOBILITY SPECTROMETERS USING TRAPPED IONS

(75) Inventors: Melvin Andrew Park, Billerica, MA (US); Desmond Allen Kaplan, Billerica, MA (US); Mark Ridgeway, Bremen (DE)

(73) Assignees: Bruker Daltonics, Inc., Billerica, MA (US); Bruker Daltonik, GmbH, Bremen (DE)

( * ) Notice: Subject to any disclaimer, the term of this patent is extended or adjusted under 35 U.S.C. 154(b) by 216 days.

(21) Appl. No.: 13/094,102

(22) Filed: Apr. 26, 2011

(65) Prior Publication Data

US 2012/0273670 A1 Nov. 1, 2012

(51) Int. Cl.
*H01J 49/26* (2006.01)

(52) U.S. Cl.
USPC ............................. 250/288; 250/281; 250/282

(58) Field of Classification Search
USPC .................. 250/281, 282, 288, 289, 290, 294
See application file for complete search history.

(56) References Cited

U.S. PATENT DOCUMENTS

| | | | |
|---|---|---|---|
| 6,803,567 B2 | 10/2004 | Leonhardt | |
| 7,838,826 B1 | 11/2010 | Park | |
| 7,902,501 B2 | 3/2011 | Landgraf | |
| 2002/0113207 A1 | 8/2002 | Lee | |
| 2010/0090102 A1* | 4/2010 | Rather et al. | 250/283 |

FOREIGN PATENT DOCUMENTS

| | | |
|---|---|---|
| GB | 2419462 A1 | 4/2006 |
| GB | 2463149 A1 | 3/2010 |
| GB | 2464774 A | 5/2010 |
| GB | 2473723 A1 | 3/2011 |
| GB | 2490387 A1 | 10/2012 |

\* cited by examiner

*Primary Examiner* — Nicole Ippolito
*Assistant Examiner* — Hanway Chang
(74) *Attorney, Agent, or Firm* — Robic, LLP

(57) ABSTRACT

In an ion mobility spectrometer in which a gas flows through a gas-tight tube with a radially quadrupolar RF field therein and blows ions against a DC electric field barrier, a mobility scan with a mobility scale that is linear in time is obtained by holding the height of the DC electric field barrier constant while changing the pressure and temperature conditions of the flowing gas. Alternatively, the mobility scan is performed by holding the pressure and temperature conditions of the flowing gas constant and reducing the height of the DC electric field barrier non-linearly with respect to time.

11 Claims, 2 Drawing Sheets

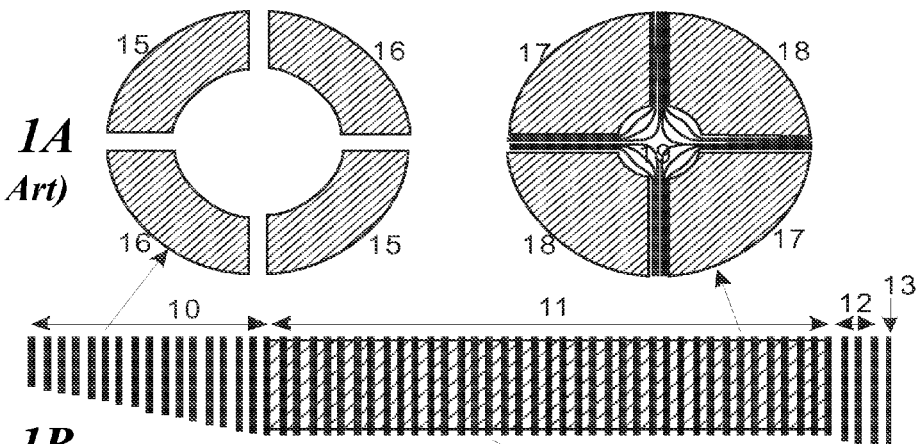
FIG. 1A
(Prior Art)
FIG. 1B
(Prior Art)
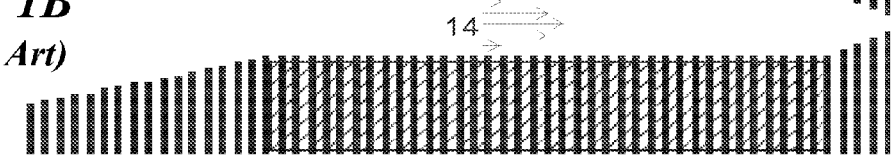
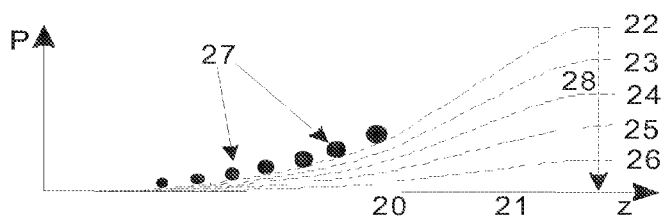
FIG. 1C
(Prior Art)
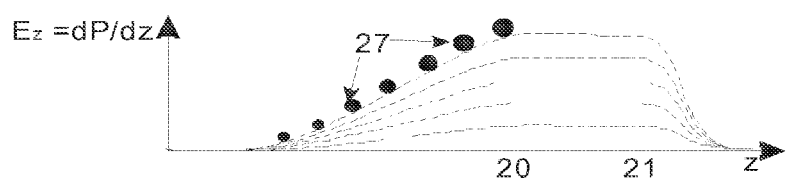
FIG. 1D
(Prior Art)

SPECTRUM ACQUISITION MODES FOR ION MOBILITY SPECTROMETERS USING TRAPPED IONS

BACKGROUND

The invention relates to devices and methods for the acquisition of ion mobility spectra in ion mobility spectrometers which apply gas flows to push ions against and over DC electric field barriers. Mass spectrometers can only ever determine the ratio of the ion mass to the charge of the ion. Where the terms "mass of an ion" or "ion mass" are used below for simplification, they always refer to the ratio of the mass m to the dimensionless number of elementary charges z of the ion. This charge-related mass m/z has the physical dimension of a mass; it is often also called "mass-to-charge ratio", although this is incorrect with regard to physical dimensions. "Ion species" shall denote ions having the same elemental composition, the same charge and the same three-dimensional structure. Ion species generally comprise all the ions of an isotope group, which consist of ions of slightly different masses, but virtually the same mobilities.

Different kinds of isomers are known for bioorganic molecules: isomers related to the primary structure (structural isomers) and isomers related to the secondary or tertiary structure (conformational isomers). Isomers have different geometrical forms but exactly the same mass. It is therefore impossible to differentiate between isomers on the basis of their mass. Some information as to the structure can be obtained from fragment ion mass spectra; however, an efficient and certain way to recognize and distinguish such isomers is to separate their ions according to their different mobilities.

Nowadays, the mobility of ions is most often measured via their drift velocities in a stationary gas under the influence of an homogeneous electric field. A drift region is filled with an inert gas such as helium, nitrogen or argon. The ions of the substance under investigation are pulled through the gas by means of the electric field, which is produced by suitable DC potentials applied to ring electrodes arranged along the drift region. The friction with the gas results in a constant drift velocity $v_d$ for each ion species which is proportional to the electric field strength E: $v_d = \mu \times E$. The proportionality factor $\mu$ is called the "ion mobility" of the ion species. The ion mobility $\mu$ is a function of gas temperature, gas pressure, type of gas, ion charge and, in particular, the collision cross-section of the ions.

Isomeric ions with the same charge-related mass m/z but different collision cross-section have different ion mobilities in a gas of the same temperature, pressure and type. Isomers of the smallest geometric dimension possess the greatest mobility and therefore the highest drift velocity $v_d$ through the gas. Unfolded protein ions undergo more collisions than tightly folded proteins. Protein ions which are unfolded or partially folded therefore arrive at the end of the drift region later than strongly folded ions of the same mass. But structural isomers, for example proteins with glycosyl, lipid or phosphoryl groups at different sites, also have different collision cross-sections, which allow them to be distinguished by measuring their ion mobility.

In chemical and biological research, it has become more and more important to have knowledge about the folding structures of ions, which can be identified via their mobility. Therefore devices to measure the mobility of ions have been incorporated into mass spectrometers, in particular, in order to combine the measurements of the charge-related mass of ions with the measurement of collision cross-sections. The folding structures determine the mechanism of action and thus the function of the molecules in the living organism; different foldings can signify normal or abnormal functioning of biopolymers in biosystems, and hence health or disease of tissue parts or even whole organisms.

A number of academic research groups have coupled ion mobility spectrometers of the drift tube type with mass spectrometers. A pressure range of several hectopascals has been adopted almost universally for the mobility drift region. In this pressure range, the drifting ions appear to form hardly any complexes with other substances, so the mobilities of the ion species can be measured without interferences, unlike mobility measurements at atmospheric pressure where quite often complex ions are formed with impurity molecules in the gas. The drift region for higher mobility resolutions measures up to four meters and more, and electric field strengths of 2,000 volts per meter and more are applied. But in the long drift regions, the ions also diffuse radially over long distances, and therefore quite large diameters have to be chosen for these drift regions.

The ions are usually introduced into the drift region in the form of temporally short ion pulses by a gating device, producing spatially small ion clouds, which are pulled through the drift region by the electric field. In the gas of the drift region, these ion clouds are subject to diffusion into all directions, caused by their Brownian motion (Boltzmann distribution). The diffusion acts equally in all directions; it takes place as well in forward and backward direction as at all angles to the drift direction. The gas in the drift region is sometimes kept at temperatures of between about 150 and 300 degrees Celsius, but can also be greatly cooled for special experiments.

The mobility resolving power ("mobility resolution" for short) is defined as $R_{mob} = \mu/\Delta\mu = v_d/\Delta v_d$, where $\Delta\mu$ is the width of the ion signal of the mobility $\mu$ at half height, measured in units of ion mobility, and $\Delta v_d$ is the corresponding difference in speed. The mobility resolution $R_{mob}$ is influenced predominantly by the diffusion broadening of the ion clouds, especially for long drift regions and high electric field strengths; all other influences, such as the space charge, tend to be negligibly small. The part of the mobility resolution Rd determined by the diffusion broadening is given by the equation $$R_d = \sqrt{\frac{zeEL_d}{kT\ln 2}},$$

where z is the number of elementary charges e, E the electric field strength, $L_d$ the length of the drift region, k the Boltzmann constant and T the temperature of the gas in the drift region. A high mobility resolution for an ion with a given number z of elementary charges e can thus only be achieved by means of a high field strength E, a long drift region $L_d$, or a low temperature T. The part Rd of the mobility resolution that is given by the diffusion is not dependent on either the type or pressure of gas in the drift region; the mobility $\mu$ itself, however, does depend not only on the temperature, but also on the pressure and type of gas.

Compared to the numerical values for mass resolutions in mass spectrometry, which can be up to several ten thousand, the mobility resolutions which can be achieved in practice are generally very low. The first commercial combination of an ion mobility spectrometer and a mass spectrometer for bioorganic ions has a maximum mobility resolution of only $R_{mob} = 40$. With a mobility resolution of $R_{mob} = 40$, two ion species whose collision cross-sections differ by only five percent can be separated very well.

Only highly specialized groups of scientists have, as yet, been able to achieve significantly higher mobility resolutions than $R_{mob}=100$, in rare individual cases up to $R_{mob}=200$, with drift lengths roughly between two and six meters and field strengths between 2,000 and 4,000 volts per meter, making it possible to differentiate between ion species whose mobilities differ by only one to two percent. Ion mobility spectrometers with a resolution above $R_{mob}=100$ shall be regarded as "highly resolving" here.

As mentioned above, in long mobility drift regions also a strong transverse diffusion occurs. Therefore, longer drift regions must also have a large diameter so that the ions do not touch the wall electrodes. A well-tried method is to guide the ions back to the axis of the drift region after they have passed through a part of the drift region, about two meters, for example. This is done using so-called "ion funnels". These consist of a larger number of parallel ring diaphragms, a small distance in the order of millimeters apart, whose aperture diameters taper continuously from the diameter of the drift region, 30 to 40 centimeters, for example, down to around two to five millimeters and thus form a funnel-shaped enclosed volume. The two phases of an RF voltage, usually of several megahertz and between a few tens of volts and one hundred volts, are applied alternately to the apertured diaphragms, thus generating a pseudopotential which keeps the ions away from the funnel wall. A DC electric field is superimposed on the RF voltage by a DC voltage gradient, and this electric field pushes the ions slowly to the narrow exit of the funnel and through it. Such an ion funnel does not measurably reduce the mobility resolution of a long drift region.

Ion funnels are not only used to guide the ions back to the axis of the drift regions in ion mobility spectrometers; they are also used in mass spectrometers in general to capture larger ion clouds and to thread these ion clouds into narrow ion guides. Such ion funnels are often found in mass spectrometers with electrospray ion sources; the ions generated outside the vacuum system are transferred, together with a curtain gas, through inlet capillaries and into the vacuum, where they are captured by ion funnels and freed of most of the curtain gas. Some mass spectrometers even contain two such ion funnels, placed in series, in order to move the ions quickly from regions with higher pressure of several hectopascals at the end of the inlet capillary to regions with lower pressure of around $10^{-2}$ to $10^{-6}$ pascal.

High-resolution time-of-flight mass spectrometers with orthogonal injection of the ions (OTOF-MS), in particular, have proven successful for combinations of mobility spectrometers with mass spectrometers. For such combinations, the high-resolution ion mobility spectrometers of the current type have the disadvantage of being several meters long. Such a solution is unfavorable for instruments marketed commercially. Even ion mobility spectrometers with a straight drift region offering only moderate resolution are about one meter long. For the construction of small, high-resolution mobility analyzers, one therefore has to look for a solution which shortens the overall length but does not diminish the mobility resolution.

In document U.S. Pat. No. 7,838,826 B1 (M. A. Park, 2008), an ion mobility spectrometer is presented, the size of which amounts to about ten centimeters only. It is based upon moving gases driving ions over an electric counter-field barrier in a modified ion funnel built into a time-of-flight mass spectrometer. Unlike many other trials to build small ion mobility spectrometers, the device by M. A. Park has already achieved ion mobility resolutions in excess of $R_{mob}=100$.

The apparatus of M. A. Park and its operation is schematically illustrated in FIGS. 1A to 1D. FIG. 1B shows, how the parts (10) and (12) of a quadrupolar funnel, open as usual to the flow of gas between the electrodes, are separated by a closed quadrupole device (11), vertically sliced into thin electrodes (17, 18 FIG. 1A) forming a circular tube arranged around the z-axis of the device. The electrode slices are separated by insulating material closing the gaps between the electrodes around the tube to make the tube gas-tight. FIG. 1A shows the shape perpendicular to the device axis (denoted as the z-axis) of the electrodes of the funnel (15, 16) and shapes perpendicular to the device axis of the quadrupole tube electrodes (17, 18), the latter with equipotential lines of the quadrupolar RF field inside the tube at a given time. The differential pumping system of a mass spectrometer (not shown), surrounding the ion mobility spectrometer, is dimensioned to cause a gas to flow through the tube (11) in a laminar way, thereby causing the flow to assume the usual parabolic velocity profile (14). Ions entering the first part (10) of the funnel together with the gas are collisionally focused onto the axis of the tube (11) and move, driven by the gas, along the axis of the tube towards its exit through the apertured diaphragm (13). Most of the gas escapes through gaps between the electrodes of the funnel part (12).

A funnel (10) or (12) usually is operated with apertured diaphragms the openings of which taper to smaller diameters thus forming an inner volume in the shape of a funnel. The two phases of an RF voltage are applied alternately to the diaphragms to build up a pseudopotential which keeps the ions away from the funnel walls. The ion funnel entrance part (10) is here built from electrodes which are divided into four parts to allow a more complicated RF field to be applied, but this is not essential for the operation of this ion mobility spectrometer.

FIGS. 1C and 1D show, in two diagrams, different DC potential profiles P (22 to 26) along the z-axis, and corresponding barriers of the electric counter field $E_z=dP/dz$ along the z-axis, respectively. The potential profiles are produced, as usual, by a network of resistors with exactly chosen values between the electrode slices, operating as voltage dividers. In this way, only a single voltage has to be applied and forms the complete profile; changing this voltage changes the potential profiles (22 to 26) as a whole.

The operation of the ion mobility spectrometer will be described by the sequence in which the potential profiles are changed. The operation starts with a filling process. The steepest potential profile (22) is generated by a voltage in the order of 100 to 200 volt, producing the highest electric field barrier. The ions (27) are blown by the gas flow against the field barrier and are stopped there because they cannot surmount the field barrier. Ions with high mobility (small cross section) gather at the foot of the barrier, ions with low mobility gather (large cross section) near the summit, as symbolically indicated by the size of the dots for the ions (27). When a suitable number of ions are collected, further ions are prevented from entering the ion mobility spectrometer, for instance, by changing the voltage gradient in the ion funnel (10). Then, for a spectrum acquisition, the potential profile (22) is smoothly lowered by decreasing the voltage continuously in a procedure denominated as a "scan" (28), passing through profile states (23) to (26). During the scan, ions of higher and higher mobilities can surmount the decreasing summit of the barrier and exit the ion mobility spectrometer. The exiting ions are measured by an ion detector, favorably a mass spectrometer. The measured ion current curve presents directly the ion mobility spectrum from low ion mobilities to high ion mobilities. This device is denominated a "TIMS", or "trapped ion mobility spectrometer".

As shown in FIG. 1D, a characteristic feature of this instrument is the long increasing part of the electric field barrier until position (20), the start of the plateau. This long ascent between foot and top of the barrier collects the ions (27) in a rather large volume along the z-axis, reducing greatly any space charge effects.

Another characteristic feature of this instrument is the flat plateau of the electric field barrier height between positions (20) and (21) on the z-axis. If the barrier is lowered slowly during an acquisition, ions have to dwell, for a few milliseconds while passing over the flat plateau, in a critical balance between the pushing force of the gas friction and the retarding force of the electric counter field, before they are finally blown from the end of the plateau into weaker field regions. In these few milliseconds, the high number of gas collisions causes a statistically equal selection of all ions of the same mobility, resulting in the high mobility resolution. The flat plateau of the electric barrier between positions (20) and (21) is generated by a number of resistors with exactly equal resistance in the resistor chain of the voltage divider.

With this instrument, the ion mobility resolution $R_{mob}$ was found to increase with increasing pressure and with decreasing acquisition speed. Furthermore, the mobility resolution $R_{mob}$ was found to be a function of the mobility $\mu$ itself: with linearly decreasing voltage, the mobility resolution $R_{mob}$ decreases from lower to higher mobilities $\mu$. It is to be expected that the mobility resolution $R_{mob}$ will depend also on gas velocity $v_g$ in connection with changes of the height of the electric barrier; the type of gas should also play a role. The rather small device turns out to be as good as long drift tubes with resting gas described above which also have to be operated in measuring phases started by pulses of ions which have to be collected first. Ion mobilities in excess of $R_{mob}$=100 have been achieved with the small apparatus in first experiments.

As operated hitherto, the device still shows a disadvantage. If during a scan (28) the voltage decreases linearly, the mobility spectrum is not linear in mobility or in resolution. Linearity in mobility, however, is advantageous for any calibration and the necessary interpolations.

SUMMARY

In accordance with the principles of the invention, the linear scan method of the ion mobility spectrometer as described in U.S. Pat. No. 7,838,826 is modified to be a non-linear function of time.

A first embodiment generates a linear mobility spectrum by decreasing the field strength, $E_z$, of the electric barrier as a function of time t in a hyperbolic scan function $E_z(t)=c/t$, (c is a constant) while keeping the gas velocity, $v_g$, constant. Surprisingly, not only a linear mobility scale is achieved, this acquisition mode also generates ion mobility spectra with much better constancy of the resolution than the acquisition modes with linear scans applied hitherto.

A second embodiment scans the field strength of the electric barrier relatively slowly over a predetermined range of interest, but comparatively rapidly over ranges outside the range of interest. This increases the mobility resolution within the range of interest without sacrificing the speed of analysis.

In a third embodiment, the field strength $E_z$ is scanned as an exponential function of time, $E_z(t)=c\, e^{-t/\tau}$ resulting in a spectrum having a fixed resolution versus mobility. These embodiments do not require any modification of the hardware, only the control software has to be changed to allow for the non-linear application of the DC voltage generating the electric barrier.

Other embodiments change the gas flow conditions. In one embodiment the gas velocity, $v_g$, is linearly increased while keeping the profile of the electric counter field constant, also resulting in an ion mobility spectrum with a linear spectrum scale. In another embodiment, the gas pressure p is increased. Both these latter spectrum acquisition embodiments require the introduction of new gas supply lines for the control of gas speed and gas pressure, and some modifications of the differential pumping system. These new gas supply lines also allow for the introduction of special gases in order to replace the primary ion transport gas by more favorable gases like helium or argon.

BRIEF DESCRIPTION OF THE DRAWINGS

FIGS. 1A to 1D schematically illustrate design and operation of an ion mobility spectrometer according to the state of the art, as described in U.S. Pat. No. 7,838,826 B1 (M. A. Park, 2008).

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

Figure 2A:
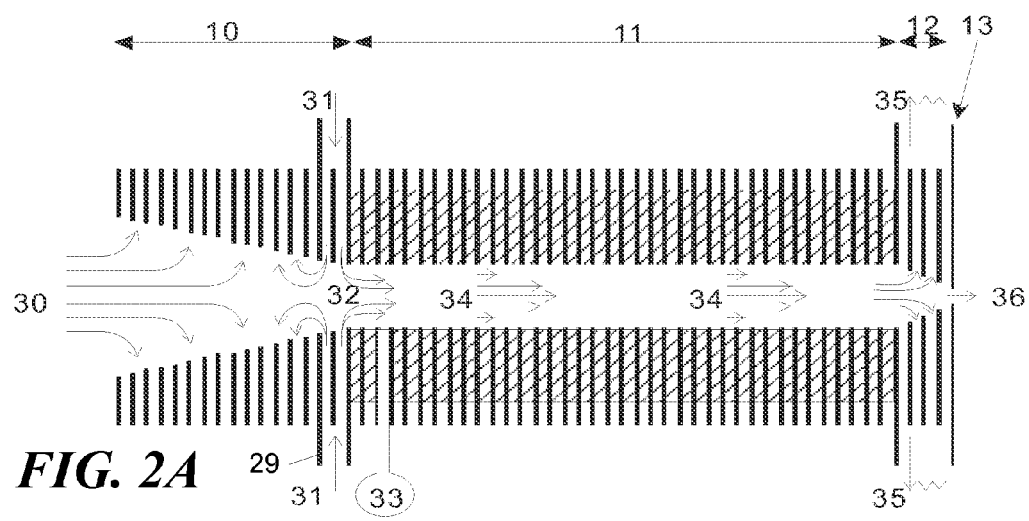
FIGS. 2A to 2C show some modifications of this instrument, by a controlled supply (31) of an exchange gas and a manometer (33), enabling operation at different gas pressures and with different types of gas, and particularly offering a mobility acquisition by continuously increasing the gas velocity $v_g$ or gas pressure p.
Figure 2B:
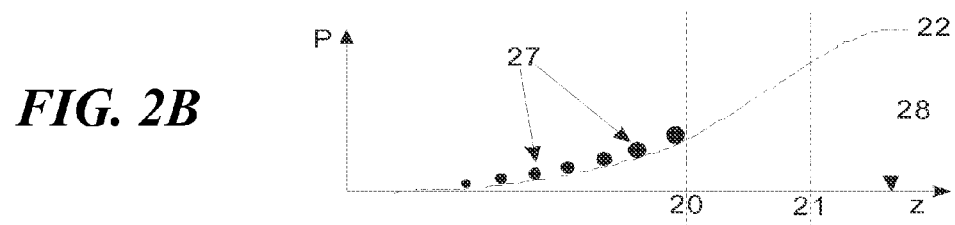
Figure 2C:
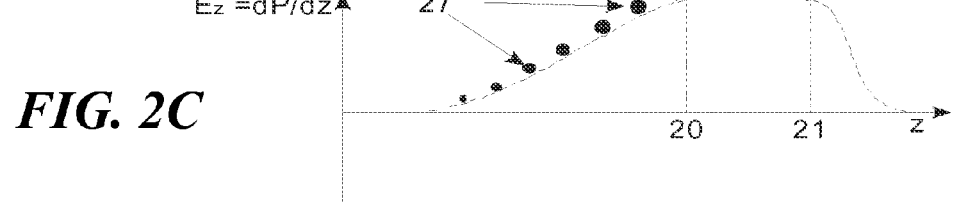

As mentioned above, the present invention is based on the ion mobility spectrometer as described in document U.S. Pat. No. 7,838,826 B1 (M. A. Park, 2008) and schematically illustrated in FIGS. 1A-1D. The invention provides several new spectrum acquisition methods with different types of benefits, some of them delivering spectra on a linear mobility scale, surprisingly showing at the same time much better constancy in ion mobility resolution. Some of these new acquisition methods require modifications of the gas guidance in the instrument, as shown in FIGS. 2A-2C.

A first set of new ion mobility spectrum acquisition methods applies non-linear electrical scans, i.e., non-linear changes (28) of the height $E_z$ of the electric barrier with time t.

A first embodiment of this set of non-linear electrical scans (28) generates a linear mobility spectrum by essentially decreasing the field strength, $E_z$, with time t in a hyperbolic scan function $E_z(t)=c/t$ (c being a constant), while keeping the gas velocity $v_g$ and pressure p constant. The decrease of the voltage starts moderately fast and slows down during the acquisition, improving resolution for ions of higher mobility. This new acquisition embodiment thus not only generates ion mobility spectra with linear scale, but at the same time with much better constancy of the resolution than the acquisition modes applied hitherto. For an ion mobility spectrum acquisition, the equation $\mu(t)=v_g/E(t)$ holds, $v_g$ being the gas velocity. With the hyperbolic scan function $E_z(t)=c/t$, the mobility $\mu$ shows a linear variation with time: $\mu(t)=v_g t/c$, i.e., the mobility scale becomes linear in time t. This acquisition embodiment does not require any modification of the hardware, only the control software has to be changed to allow for this non-linear scan of the DC voltage generating the electric barrier.

An acquisition embodiment resulting in a mobility spectrum on a linear mobility scale is of some value for the calibration of the ion mobility spectrum. With a linear mobility scale, only a few calibration points, obtained with calibrant substances of precisely known ion mobilities, are sufficient for a good calibration. A calibrated acquisition method allows the mobility values for unknown substances to be easily read, even by extrapolation for some distance outside the calibrated region.

A second embodiment with non-linear changes (28) of the electric field barrier $E_z$ scans the field strength $E_z(t)$ of the electric barrier relatively slowly over a predetermined range of interest, but comparatively rapidly over ranges outside the range of interest. This increases the mobility resolution within the range of interest without sacrificing the speed of analysis. If highest acquisition rates are to be achieved, and the interest is concentrated in a small region of mobilities only, this "zoom scan" may be applied. A zoom scan consists of three phases: a first partial scan with highest scan speed, a second "zoom" phase with a reduced scan speed for highest resolution, and a third phase with fast scan speed to empty the trap. In most cases, the ion mobilities outside the zoom range are not of interest at all; so these ions do not need to be measured. The zoom scan shortens the acquisition time considerably, and thus increases the acquisition rate. In a slightly altered variant of this zoom scan, the filling process is performed with a barrier height which allows ions of low mobility outside the window of interest to pass. The acquisition can then be started directly with the zoom phase of reduced scan speed.

In a third embodiment with non-linear electrical scans, the field strength $E_z$ is scanned as an exponential function, $E_z(t)=c\ e^{-t/\tau}$ resulting in a spectrum having a fixed resolution versus mobility. This exponential scan can be easily achieved by discharging a capacitor to deliver the voltage for the electric DC field barrier.

Unless the voltage for the third embodiment is generated by a discharging a capacitor, these three new acquisition embodiments with non-linear scans do not require any modifications of the hardware, only the control software has to be changed to allow for non-linear DC voltage scans with time, generating non-linear changes of the electric barrier $E_z$.

A second set of new acquisition embodiments change the gas flow conditions, requiring the introduction of a new gas supply means for the control of gas pressure and/or gas velocity, as shown in FIG. 2A, possibly including some modifications of the differential pumping system.

A first new acquisition embodiment changing gas flow conditions increases the gas velocity $v_g$ while keeping constant the gas pressure p, and the height and profile of the electric counter $E_z(z)$ field. With a linear increase of gas velocity $v_g$, the acquisition embodiment also produces linear ion mobility spectra, and a somewhat better constancy of the resolution along each spectrum. This acquisition embodiment requires the control of the gas velocity $v_g$, by control of the gas flows (31), (32), (34), (35), and (36) in FIG. 2A. This control requires the introduction of new gas supply means (not shown in FIG. 2A), and some modifications of the differential pumping system to be able to take up and control the gas flows (35) and (36) exiting the ion mobility spectrometer.

If there is not only a control of the incoming gas flow (31), but also of the exiting gas flows (35) and (36), the pressure p of the gas inside the tube (11) may be controlled. A manometer (33) may be used to measure the gas pressure p continuously. The gas pressure p has a great influence on the ion mobility resolution $R_{mob}$: the higher the pressure p, the better the resolution $R_{mob}$. With these new gas supply means, it is now possible to change the pressure p of the gas continuously and to produce a "pressure scan". A second new acquisition embodiment for ion mobility spectra by changing the gas flow conditions, therefore, utilizes an increase of the pressure p, preferably in a linear mode, while keeping the other acquisition parameters $E_z$ and $v_g$ constant.

Whereas all the ion mobility spectrum acquisition embodiments described here keep constant some of the acquisition parameters $E_z$, $v_g$, and p, a further acquisition embodiment has a combined scan of the height $E_z$ of the electric DC field barrier, the velocity $v_g$ and the pressure p of the gas, all three acquisition parameters in any time dependence.

With the new gas supplies, also special gases may be introduced in order to at least partially replace the ion transport gas (30) driving the ions from the ion source to the first part (10) of the ion funnel, even without using the acquisition embodiment with varying gas velocity $v_g$. This ion transport gas (30) in most cases consists of nitrogen introduced into the vacuum system by atmospheric pressure ion sources, for instance, by an electrospray ion source. It may be replaced by monoatomic gases (31) like helium or argon which are more favorable for comparisons of measured mobility values with theoretical calculations. But the replacement of the ion transport gas (30) may also be used to increase the mobility resolution, particularly, when the replacement gas flow (31) is cooled to low temperatures.

Besides offering gas flow velocity control, the replacement of the ion transport gas (30) by a replacement gas (31) has other advantages, even if the replacement gas (31) is identical in type with the ion transport gas (30). Replacing the gas keeps neutral molecules of chemical contaminations and neutral solvent molecules from entering the tube (11), which may disturb the measurements of the ion mobility.

In alternate embodiments, part (10) may be comprised of electrodes which are contiguous, ring shaped electrodes rather than sliced electrodes. In other alternate embodiments, the inner surface of part (10) formed by the electrodes may have a steeper or shallower funnel shape. Electrode (29) at the outlet of part (10) may have an aperture diameter smaller than that of part (11) such that the fraction of gas flow (32) which flows upstream may be restricted relative to downstream flow (34). In further alternate embodiments, the outlet of part (10) may be comprised of a multitude of apertured electrodes, the gaps between which are closed with insulators, forming a tubular stacked plate RF ion guide. A DC electric field gradient may be used to push ions downstream while the tubular structure restricts gas flow (32) upstream. In further alternate embodiments, part of gas flow (31) may be derived from gas flow (35). "Recycling" the gas from flow (35) in this way is especially advantageous in cases where the introduced gas is expensive.

In total, the invention provides different kinds of acquisition embodiments showing advantageous features. Acquisition embodiments with linear scales for ion mobilities μ and better constancy for the resolution $R_{mob}$ along the spectrum can be achieved. Measuring the ion mobilities in gases different from the transport gases shows advantages and even may increase resolution. With the application of the acquisition embodiments of this invention, ion mobility spectra with resolutions by far exceeding $R_{mob}=100$ are to be expected, the resolution being almost constant along the ion mobility spectrum.

What is claimed is:

1. A method for acquiring an ion mobility spectrum of ions, comprising:
   (a) providing an ion mobility spectrometer in which a gas flows through a gas-tight tube having a radially quadrupolar RF field therein and blows the ions against a DC electric field barrier, the gas flow having a parabolic velocity profile within the tube; and
   (b) changing conditions of the flowing gas with time at the location of the DC electric field barrier while acquiring the ion mobility spectrum.

2. The method of claim 1, wherein in step (b), the velocity $v_g$ of the flowing gas is increased from a low velocity to a higher velocity.

3. The method of claim 2, wherein the velocity $v_g$ is increased linearly.

4. The method of claim 1, wherein in step (b), the pressure p of the gas is increased from a low pressure to a higher pressure.

5. The method of claim 1 wherein, in step (b), the temperature and pressure conditions of the flowing gas are changed to acquire the ion mobility spectrum.

6. A method for acquiring an ion mobility spectrum of ions, comprising:
   (a) providing an ion mobility spectrometer, in which a gas flows through a gas-tight tube with a radially quadrupolar RF field therein and blows the ions against a DC electric field barrier, the gas flow having a parabolic velocity profile within the tube; and
   (b) decreasing the height of the DC electric field barrier non-linearly with time to acquire the ion mobility spectrum.

7. The method of claim 6, wherein in step (b) the height of the DC electric field barrier is decreased substantially inversely proportionally with respect to time.

8. The method of claim 6, wherein in step (b), the height of the DC electric field barrier is decreased substantially by an exponential function $e^{-t/T}$ of time t.

9. The method of claim 6, wherein in step (b), the height of the electric DC field barrier is decreased with a first speed in a first time interval, with a second speed in a second time interval, and with third speed in a third time interval, wherein the third speed is higher than the first and the second speeds.

10. An ion mobility spectrometer comprising:
    a gas-tight tube;
    a gas source that generates a gas that flows in the tube from a tube entrance to a tube exit with a parabolic velocity profile;
    a voltage generator that generates a radially quadrupolar RF field and an DC electric field barrier in the tube; and
    means for varying at least one of the pressure p and the velocity $v_g$ of the gas flow with time at the location of the DC electric field barrier while acquiring an ion mobility spectrum.

11. The ion mobility spectrometer of claim 10, further comprising a second gas source that introduces a secondary gas flow at the tube entrance, whereby the gas flow which transports ions to the tube is at least partially replaced by the secondary gas flow.

* * * * *